United States Patent [19]

Veronesi et al.

[11] Patent Number: 6,087,338

[45] Date of Patent: Jul. 11, 2000

[54] PHARMACEUTICAL NON INORGANIC SALINE SOLUTIONS FOR ENDONASAL ADMINISTRATION OF A CALCITONIN

[75] Inventors: Paolo Alberto Veronesi; Emanuela Peschechera, both of Milan; Anna Maria Veronesi, Umbra, all of Italy

[73] Assignee: Therapicon S.R.L., Milan, Italy

[21] Appl. No.: 08/908,986

[22] Filed: Aug. 8, 1997

Related U.S. Application Data

[63] Continuation of application No. PCT/EP96/00446, Feb. 8, 1996.

[30] Foreign Application Priority Data

Feb. 8, 1995 [EP] European Pat. Off. .............. 95101681

[51] Int. Cl.$^7$ .................................................. A61K 38/23
[52] U.S. Cl. ............................................ 514/21; 530/307
[58] Field of Search ............................... 514/21; 530/307

[56] References Cited

U.S. PATENT DOCUMENTS

| | | |
|---|---|---|
| 4,690,952 | 9/1987 | Kagatani et al. . |
| 5,026,825 | 6/1991 | Grebow et al. . |
| 5,183,802 | 2/1993 | Aliverti et al. . |
| 5,571,788 | 11/1996 | Arvinte et al. . |
| 5,733,569 | 3/1998 | Azria et al. . |

FOREIGN PATENT DOCUMENTS

| | | |
|---|---|---|
| 0 122 036 A1 | 10/1984 | European Pat. Off. . |
| 0 358 234 A3 | 3/1990 | European Pat. Off. . |
| 0358234 A2 | 3/1990 | European Pat. Off. . |
| 0 490 549 A1 | 6/1992 | European Pat. Off. . |
| 0 504 483 A1 | 9/1992 | European Pat. Off. . |
| 0327756 B1 | 1/1994 | European Pat. Off. . |
| 3335086 | 9/1990 | Germany . |
| 2127689 | 4/1984 | United Kingdom . |
| WO 93/06854 | 4/1993 | WIPO . |
| WO 96/24618 | 8/1996 | WIPO . |
| WO9624370 | 8/1996 | WIPO . |

OTHER PUBLICATIONS

Sato et al., "Stabilization of Injection Solutions Containing [ASM 1,7] Callitonin" Caplus ABS # 1994:280287, Feb. 8, 1994.

Ogiso, "Topilar Solutions Containing Calcitonin as Absorption Accelerator" Caplus ABS # 1992:476537, 1992.

U.S. Pharmacopeia "Official Jan. 1, 1995" V. 23, NF18 (Defining "K–Value" for Povidone).

"Calcitonin (Salmon)" *European Pharmacopoeia* (1997) pp. 508–511, published in Europe.

Bruynzeel, DP et al. "Contact dermatitis to lauryl pyridinium chloride and benzoxonium chloride" *Contact Dermatitis* (1987) vol. 17, pp. 41–60, published in Europe.

Fisher, A. "Allergic Contact Dermatitis and Conjunctivitis from Benzalkonium Chloride" *Cutis* (May 1987) vol. 39, pp. 381–383.

Lee, KC et al. "Degradation of Synthetic Salmon Calcitonin in Aqueous Solution" *Pharmaceutical Research* (1992) vol. 9, No. 11, pp. 1521–1523.

Lemp, MA and LE Zimmerman. "Toxic Endothelial Degeneration in Ocular Surface Disease Treated with Topical Medications Containing Banzalkonium Chloride" *American Journal of Ophthalmology*, (Jun. 1988) vol. 105, pp. 670–673, published in US.

Chemical Abstracts 98: 204410s, Larsen et al., 1983.
Chemical Abstracts 118: 66873y, Sims et al., 1993.
Chemical Abstracts 118: 198207u, Santus et al., 1993.
Chemical Abstracts, vol. 117, No. 10, Sep. 7, 1992, Columbus, Ohio, US; Abstract No. 97319, Nogata, Yoshihiko et al.: "Aqueous Compositions Containing Calcitonins" XP002005905.

Database WPI, Section Ch., Week 9211, Derwent Publications Ltd., London, GB; Class B04, AN 92–85873, & JP,A,04 029 938 (Toyo Jozo KK), Jan. 31, 1992.

Patent Abstracts of Japan, vol. 16, No. 194 (C–938), May 11, 1992 & JP,A,04 029938 (Toyo Jozo Co Ltd.), Jan. 31, 1992.

*Primary Examiner*—Johann Richter
*Assistant Examiner*—Patrick R. Delaney
*Attorney, Agent, or Firm*—Steven P. Shurtz; Brinks Hofer Gilson & Lione

[57] ABSTRACT

The subject-matter of the invention are pharmaceutical non inorganic saline solutions for endonasal administration containing: (a) a calcitonin, preferably salmon or alternatively carbacalcitonin (elcatonin), or its pharmaceutically acceptable salts; characterized in that it further contains the organic excipients; (b) N-(methyl)-glucamine or glucamine; (c) tromethamine; (d) citric acid; and (e) polyvinylpyrrolidone ranging from K15 to K120. These are odorless and tasteless and thus have improved patient's compliance not having the undesirable secondary effects of known compositions as well as permit a complete and accurate analysis of the active principle and develop less degradation products during storage.

25 Claims, No Drawings

PHARMACEUTICAL NON INORGANIC SALINE SOLUTIONS FOR ENDONASAL ADMINISTRATION OF A CALCITONIN

CROSS REFERENCE TO RELATED APPLICATION

This application is a continuation of PCT Application Ser. No. PCT/EP96/00446 filed Feb. 8, 1996, designating the United States of America.

The invention is concerned with novel pharmaceutical non saline solutions for endonasal administration containing a natural or modified calcitonin, more preferably salmon calcitonin or carbocalcitonin (elcatonin), having enhanced organoleptic characters and a better patient's compliance.

Calcitonins are well-known long chain polypeptides used for convenient prophylaxis and therapy of some diseases, like Paget's disease, hypercalcemia and osteoporosis.

Calcitonin salmon is widely and efficiently adopted for the treatment of the above indications, so that specific monographs have been included in the most qualified pharmacopoeias like Eur. Ph. II Ed., DAB 10 (1991), BP 88, F.U. IX Ed..

The above pharmacopoeias indicate that calcitonin salmon (dry active ingredient), as acetate salt, shall contain minimum 4,000 I.U. per milligram (biological assay) and not more than 10% by weight of water and not more than 15% by weight of acetic acid. Storage condition at about 4° C./8° C. is also prescribed for the powder stability.

Already there have been described saline compositions of calcitonin salmon for endonasal administration, which are stabilized with an appreciable quantity of acetic acid, but the presence of acetic acid results in the entire composition having a very unpleasant odour of acetic acid.

Additionally in these compositions it is not possible to analytically establish the exact aliquot of acetic acid included in the active ingredient calcitonin (maximum 15% by weight) and the part of acetic acid, which has been added to the formulations as stabilizing excipient.

In other previous compositions (DE-A 33 35 086), hydrochloric acid has been used to adjust the pH value of the solution. This practice is also very inconvenient because of hydrochloric acid is able to remove acetic acid from the calcitonin acetate salt, thus producing an undesired liberation and odour of acetic acid.

Other publications teach that aliquots of calcitonins, for endonasal administration, therapeutically bioequivalent to those administered by parenteral route, are normally absorbed through the nasal mucosa and are also generally well tolerated. Calcitonins, specifically calcitonin salmon, as acetate salt, is remarkably unstable and, when it is not suitably formulated (bacterial contamination, unsuitable pH values, packed in non nitrogen atmosphere) or stored at temperatures above 8° C., it may develop some degradation products, which have already been described by some authors in the published literature.

In fact in some compositions (DE-A 33 35 086), benzalkonium chloride is used to avoid the bacterial contamination during the storage period and/or utilization, but several studies have indicated that this preserving agent produces some undesirable secondary effects (Am. J. Ophatalmol. 105 (6) [1988] pages 670 to 673; Contact Dermatitis 17 (1) [1987] pages 41 to 42; Cutis 39 (5) [1987] pages 381 to 383).

Thus the problem underlying the present invention is to create novel pharmaceutical solutions for endonasal administration containing a natural or modified calcitonin, preferably salmon or alternatively carbocalcitonin (elcatonin), or its pharmaceutically acceptable salts, which are odourless and tasteless and thus have improved patient's compliance and which does not have the undesirable secondary effects of known compositions but which permits a complete and accurate analysis of the active principle and develops less degradation products during storage.

Surprisingly this has been attained by the present invention.

The invention is based on the surprising recognition that non inorganic saline aqueous solutions containing natural or modified calcitonin as acetate salt (active principle) and besides water only organic excipients, described in the most common pharmacopoeias, like pharmaceutically acceptable acids, bases, suspending agents and, optionally $C_{1-4}$ alkylesters of p-hydroxybenzoic acid fulfil the above requirements. Surprisingly it has been found that such a composition as defined below is very suitable for endonasal administration, when applied to the nasal mucosa and it is odourless and tasteless, properties that improve the patient's compliance. Moreover the inventive composition allows performance of a complete and accurate analysis of the active ingredient calcitonin salmon (including its volatile impurities, like acetic acid) and minimizes the development of degradation products during the ageing period.

The present invention provides pharmaceutical non inorganic saline solutions for endonasal administration containing:
a) a natural or modified calcitonin, preferably salmon or alternatively carbocalcitonin (elcatonin), as its pharmaceutically acceptable salts,
characterized in that it further contains the organic excipients described in the most common pharmacopoeias
b) N-(methyl)-glucamine [meglumine] or alternatively glucamine,
c) tromethamine,
d) citric acid
e) polyvinylpyrrolidone ranging from K15 to K120.
The active principle and the said organic excipients are dissolved in water.

Advantageously the calcitonin is human calcitonin, eel calcitonin, carbocalcitonin (elcatonin), chicken calcitonin or porcine calcitonin.

Preferred solutions according to the invention contain
a) the calcitonin or its pharmaceutically acceptable salts in concentration of 250 I.U./ml to 5,000 I.U./ml,
b) the N-(methyl)-glucamine or glucamine in concentrations of 2.0 to 5.0 mg/ml,
c) the tromethamine in concentrations of 1.0 to 4.0 mg/ml,
d) the citric acid in concentrations of 5.0 to 9.0 mg/ml and
e) the polyvinylpyrrolidone ranging from K15 to K120 in concentrations of 5 to 25 mg/ml.

It is particularly preferred that the concentration of the calcitonin or its pharmaceutically acceptable salts [a)] is from 400 I.U. to 1,200 I.U./ml.

Furthermore it is particularly preferred that the concentration of the N-(methyl)-glucamine or alternatively glucamine [b)] is from 2.5 to 4.0 mg/ml.

Moreover it is particularly preferred that the concentration of the tromethamine [c)] is 1.5 to 4.0 mg/ml.

It is also particularly preferred that the concentration of the citric acid [d)] is from 6.0 to 8.0 mg/ml.

Furthermore it is particularly preferred that the concentration of the polyvinylpyrrolidone ranging from K15 to K120 is from 8 to 15 mg/ml.

Moreover it is preferred the solutions according to the invention are sterile formulations.

According to an advantageous embodiment of the invention the solutions according to the invention contain 1 or more $C_{1-4}$ alkylester(s) of p-hydroxybenzoic acid [f)] for additional protection.

Preferably the $C_{1-4}$ alkylester(s) of p-hydroxybenzoic acid [f)] is/are methyl p-hydroxybenzoate and/or propyl p-hydroxybenzoate.

It is also preferred that the solutions according to the invention have pH values preferably of from 4.6 to 6.0.

A special particularly preferred solution according to the invention contains:

$1 \times 10^3$.U./ml of calcitonin salmon as acetate salt [a)]

3.33 mg/ml of N-(methyl)-glucamine or glucamine [b)]

2.10 mg/ml of tromethamine [c)]

6.82 mg/ml of citric acid [d)]

10.00 mg/ml of polyvinylpyrrolidone [e)]

1.00 mg/ml of methyl p-hydroxybenzoate [f)]

0.10 mg/ml of propyl p-hydroxybenzoate [f)]

976.65 mg/ml of water for injectable preparations.

A further special particularly preferred solution according to the invention contains:

$2 \times 10^3$ I.U./ml of calcitonin salmon as acetate salt [a)]

3.33 mg/ml of N-(methyl)-glucamine or glucamine [b)]

2.10 mg/ml of tromethamine [c)]

6.82 mg/ml of citric acid [d)]

10.00 mg/ml of polyvinylpyrrolidone [e)]

1.00 mg/ml of methyl p-hydroxybenzoate [f)]

0.10 mg/ml of propyl p-hydroxybenzoate [f)]

976.65 mg/ml of water for injectable preparations.

The solutions according to the invention produce minimal degradation products, during the storage period. During an ageing period of 18 months they produce, a very reduced quantity of the inactive degradation product hydroxy-calcitonin. Advantageously the inventive solutions present, after 18 months of shelf-life, a total quantity of degradation product substantially less than 5% by weight limit indicated by various pharmacopoeias (Eur. Ph. II Ed., DAB 10 (1991), BP 88, FU IX Ed.) for calcitonin salmon substance. They are very suitable for endonasal administration, when dispensed in convenient well-known delivery system.

Another more particularly preferred embodiment according to the invention contains:

400 I.U./ml of elcatonin [a]

3.33 mg/ml of N-(methyl)-glucamine or glucamine [b)]

2.10 mg/ml of tromethamine [c)]

6.82 mg/ml of citric acid [d)]

10.00 mg/ml of polyvinylpyrrolidone [e)]

1.00 mg/ml of methyl p-hydroxybenzoate [f)]

0.10 mg/ml of propyl p-hydroxybenzoate [f)]

976.65 mg/ml of water for injectable preparations

The surprising advantages of the pharmaceutical solutions according to the invention are summarized as follows:

A) The presence of citric acid [d)], which is useful to adjust the pH values to preferably from 4.6 to 6.0, allows the exact quantity of acetic acid, contained as volatile impurity in calcitonin salmon or in carbocalcitonin (elcatonin) to be determined specifically and precisely, by using conventional analytical methods described in several publications.

In fact, if acetic acid was added to the solution instead of citric acid, it would not be possible to determine, in the formulated preparation, the quantity of the volatile impurity acetic acid (maximum 15% by weight) contained in calcitonin salmon or in carbocalcitonin (elcatonin).

B) The solution according to the invention with citric acid [d)] is organoleptically more acceptable to patients who don't tolerate the unpleasant odour of acetic acid contained in some prior art compositions on the market.

C) citric acid [d)] has been partially buffered, in the solutions according to the invention, preferably to pH 4.6 to 6.0, by using suitable concentrations of tromethamine [c)] and N-(methyl)glucamine or glucamine [b)] instead of sodium acetate, which can also develop a remarkable odour of acetic acid.

D) Polyvinylpyrrolidone ranging from K15 to K120, [e)] is purposely included into the composition for endonasal administration, since surprisingly it is suitable to prolong the time of contact between the solution and the nasal mucosa for its binding properties.

E) In the solutions of the invention, the presence of preserving agents is optional, because the manufacturing process is carried out to obtain sterile formulations. Moreover the nasal bottles equipped with suitable pumps, characterized by absence of air introduction after actuation (dispensing the solution), eliminating, in this way the possible bacteria contamination, during usage. Therefore $C_{1-4}$, alkylesters of p-hydroxybenzoic acid, particularly methyl p-hydroxybenzoate and/or propyl p-hydroxybenzoate, [f)] are introduced into the solutions of the invention only for additional protection, in case of an exceptional presence of bacteria.

F) More specifically for calcitonin salmon various pharmacopoeias fix an individual limit of 5% by weight for each related substance {DAB (1991) "Verwandte Substanzen"; Eur,. Ph. II Ed. "Substances apparentees"; BP 88 "Related substances"} for calcitonin salmon powder, as acetate salt, while other publications, more specifically Pharmaceutical Research Vol. 9, N. 11, 1992 ("Degradation or Synthetic Salmon Calcitonin Aqueous Solution"—Kang Choon Lee, Yoon Joong Lee, Hyun Myo Song, Chang Ju Chun and Patrick P. DeLuca) indicate that the degradation product is only the reduced calcitonin salmon (dihydro-calcitonin) when the solution presents an acidic pH. Now surprisingly it has been found that the solutions of the invention produce only minimal degradation product during the ageing period of storage.

The described embodiments of the invention may apply also to other natural or modified calcitonin, alike human calcitonin, eel calcitonin, carbocalcitonin (elcatonin), chicken calcitonin, porcine calcitonin.

The solutions according to the invention can be administered as drops, inhaler or spray, dispensed in suitable well known delivery systems.

The invention is further illustrated by the following examples.

EXAMPLE 1

Preparation of 38,461 bottles (1.0 ml) of calcitonin salmon nasal spray 100 I.U./actuation Each actuation dispensing 100 µl of solution (100 I.U. Of active principle). 1 ml of the solution containing the following constituents:

| Ingredient | Amount |
|---|---|
| Calcitonin salmon as acetate salt | $1 \times 10^3$ I.U. |
| Glucamine | 3.33 mg |

-continued

| Ingredient | Amount |
| --- | --- |
| Tromethamine | 2.10 mg |
| Citric acid (pH 4.6 to 6.0) | 6.82 mg |
| Polyvinylpyrrolidone | 10.00 mg |
| Methyl p-hydroxybenzoate | 1.00 mg |
| Propyl p-hydroxybenzoate | 0.10 mg |
| Water for injectable preparations | 976.65 mg |

The manufacturing process is carried out with the following conventional steps:

α) 34.0 kg of water for injectable preparations are introduced in a stainless steel dissolutor.

β) In about 3 liters of water is separately prepared a solution containing:

> 80.77 g of tromethamine +
> 128.1 g of glucamine +
> 250.1 g of citric acid

γ) Once the above solution has been completely dissolved, it is added to the water in the dissolutor.

δ) Under constant and slow stirring, 384.61 g of polyvinylpyrrolidone, 38.461 g of methyl p-hydroxybenzoate and 3.846 g of propyl p-hydroxybenzoate and, finally, the remaining quantity of citric acid (12.2 g) are added to yield the pH value of 4.6 to 6.0, which is adjusted, if necessary, by adding 0.1N NaOH.

ε) Separately $38.461 \times 10^6$ I.U. of calcitonin salmon as acetate salt are dissolved in about 50 ml of solution, resulting from step γ) thus obtaining the mother solution.

ζ) Under constant and slow stirring, the mother solution of calcitonin salmon and the remaining quantity of water are added to the dissolutor to yield 38.461 kg.

All manufacturing steps from α) to ζ) are carried out under nitrogen atmosphere at positive pressure.

The obtained solution is filtered for sterilization and subsequently bottled under nitrogen atmosphere at positive pressure according to the well-known methods in the Art.

EXAMPLE 2

Preparation of 25,000 bottles (2.0 ml) of calcitonin salmon nasal spray 200 I.U./actuation Each actuation dispensing 100 μl of solution (200 I.U. of active principle). 1 ml of the solution containing the following constituents:

| Ingredient | Amount |
| --- | --- |
| Calcitonin salmon as acetate salt | $2 \times 10^3$ I.U. |
| N-(Methyl)-glucamine | 3.33 mg |
| Tromethamine | 2.10 mg |
| Citric acid (pH 4.6 to 6.0) | 6.82 mg |
| Polyvinylpyrrolidone | 10.00 mg |
| Methyl p-hydroxybenzoate | 1.00 mg |
| Propyl p-hydroxybenzoate | 0.10 mg |
| Water for injectable preparations | 976.65 mg |

The manufacturing process is carried out with the following conventional steps:

α) 45.0 kg of water for injectable preparations are introduced in a stainless steel dissolutor.

β) In about 3 liters of water a solution is separately prepared containing:

> 105.0 g of trometamine +
> 166.5 g of N-(methyl)-glucamine +
> 228.5 g of citric acid γ) After the complete dissolution of the above solution it is added to the water in the dissolutor.

δ) Under constant and slow stirring, 500.0 g of polyvinylpyrrolidone, 50.0 g of methyl p-hydroxybenzoate and 5.0 g of propyl p-hydroxybenzoate and, finally, the remaining quantity of citric acid (12.5 g) are added to yield the pH value of 4.6 to 6.0, which is adjusted, if necessary, by adding 0.1N NaOH.

ε) Separately a mother solution of calcitonin salmon as acetate salt is prepared by dissolving $1 \times 10^7$ I.U. of this active principle in about 50 ml of solution resulting from step γ).

ζ) Under constant and slow stirring, the mother solution of calcitonin salmon and the remaining quantity of water are added to the dissolutor to yield 50 kg.

All manufacturing steps from α) to ζ) are carried out under nitrogen atmosphere at positive pressure.

The obtained solution is sterilized and bottled under nitrogen atmosphere at positive pressure according to the well-known methods in the Art.

EXAMPLE 3

Preparation of 10,000 bottles (1.6 ml) of carbocalcitonin (elcatonin) nasal spray 40 I.U./actuation.

Each actuation dispensing 100 μl of solution (40 .U. of active principle).

1 ml of the solution containing the following constituents:

| Ingredient | Amount |
| --- | --- |
| Elcatonin | 400 I.U. |
| N-(Methyl)-glucamine | 3.33 mg |
| Tromethamine | 2.10 mg |
| Citric acid (pH 4.6 to 6.0) | 6.82 mg |
| Polyvinylpyrrolidone | 10.00 mg |
| Methyl p-hydroxybenzoate | 1.00 mg |
| Propyl p-hydroxybenzoate | 0.10 mg |
| Water for injectable preparations | 976.65 mg |

The manufacturing process is carried out with the following conventional steps:

α) 13.5 Kg of water for injectable preparations are introduced in a stainless steel dissolutor.

β) In about 1 liter of water is separately prepared a solution containing:

> 33.6 g of tromethamine +
> 53.3 g of N-(Methyl)-glucamine +
> 104.8 g of citric acid γ) Once the above solution has been completely dissolved, it is added to the water in the dissolutor.

δ) Under constant and slow stirring, 160.0 g of polyvinylpyrrolidone, 16.0 g of methyl p-hydroxybenzoate and 1.6 g of propyl p-hydroxybenzoate and, finally, the remaining quantity of citric acid (4.2 g) are added to yield the pH value of 4.6 to 6.0, which is adjusted, if necessary, by adding 0.1N NaOH.

ε) Separately 6.4 $10^6$ I.U. of elcatonin are dissolved in about 20.0 ml of solution, resulting from step γ) thus obtaining the mother solution.

ζ) Under constant and slow stirring, the mother solution of elcatonin and the remaining quantity of water are added to the dissolutor to yield 16 Kg.

All manufacturing steps from α) to ζ) are carried out under nitrogen atmosphere at positive pressure.

The obtained solution is filtered for sterilization and subsequently bottled under nitrogen atmosphere at positive pressure according to the well-known methods in the Art.

EXAMPLE 4

Stability study of calcitonin salmon nasal spray preparations of Examples 1 and 2

The stability study is carried out comparing the pharmaceutical solution according to the invention of Examples 1 and 2 to two formulations available on the market, in order to assess the quality and the quantity of degradation products, during an interval of 18 months at the controlled storage temperature of +2°/+8° C.

Formulations I and II are those indicated in Examples 1 and 2, while the compared formulations III and IV have the following compositions:

Formulation III 1 ml of solution containing 550 I.U. of calcitonin salmon as acetate salt, 0.002 g of glacial acetic acid, 0.002 g of sodium acetate trihydrate, 0.0075 g of sodium chloride and water for injectable preparations q.s. to 1 ml.

Formulation IV 1 ml of solution containing 550 I.U. of calcitonin salmon as acetate salt, 0.1 mg of benzalkonium chloride, 8.5 mg of sodium chloride, 4 mg of 0.1N hydrochloric acid and 990.025 mg of bidistilled water.

The obtained results are summarized in the following Table 1.

TABLE 1

| Formulation | TIME 0 (Initial) | | AFTER 18 MONTHS | |
| --- | --- | --- | --- | --- |
| | Degradation products | | | |
| | hydroxy-calcitonin % by weight | dihydro-calcitonin % by weight | hydroxy-calcitonin % by weight | dihydro-calcitonin % by weight |
| Formulation I (Example 1) | 0.11 | 0 | 1.87 | 0 |
| Formulation II (Example 2) | 0.13 | 0 | 2.14 | 0 |
| Formulation III | 0.10 | 0 | 4.31 | 2.58 |
| Formulation IV | 0.12 | 0 | 5.06 | 2.37 |

As it may be taken from the above results, the pharmaceutical formulations of the invention (I and II) generate, during the considered ageing period of 18 months, remarkably minor quantities of the degradation product hydroxy-calcitonin, compared to reference formulations III and IV which additionally produce another related substance indicated as dihydro-calcitonin (reduced calcitonin).

EXAMPLE 5

Comparative study of organoleptic characters of the pharmaceutical formulations I (according to the invention) and III (reference) of Example 4

In order to assess the tolerability and compliance of the considered preparations, a comparative double-blind study between the pharmaceutical formulation I (according to the invention) and II (reference) of Example 4 has been carried out, by administering them to a total of 20 healthy and non smoking volunteers, divided into two groups.

In phase 1 test, 10 volunteers have inhaled formulation I while the second group formulation III. Phase 2 test was carried out, after two hours interval, by administering to the first group formulation III and to the second group formulation I.

The obtained results are summarized in the following Tables 2 and 3.

TABLE 2

| | Phase 1 Test | |
| --- | --- | --- |
| Organoleptic evaluation | Formulation I | Formulation III |
| Odour of acetic acid | 0 | 7 |
| Odourless | 9 | 1 |
| No difference | 1 | 2 |

TABLE 3

| | Phase 2 Test | |
| --- | --- | --- |
| Organoleptic evaluation | Formulation I | Formulation III |
| Odour of acetic acid | 0 | 9 |
| Odourless | 8 | 0 |
| No difference | 2 | 1 |

It results from the above Tables 2 and 3 that most of the treated volunteers of the two groups (16) have reported that formulation III (reference) has a statistically significant unpleasant odour of acetic acid, while 17 volunteers have not detected any specific odour in formulation I (according to the invention).

We claim:

1. Pharmaceutical solutions for endonasal administration comprising:
   a) calcitonin or its pharmaceutically acceptable salts;
   b) N-(methyl)-glucamine or glucamine;
   c) tromethamine;
   d) citric acid; and
   e) polyvinylpyrrolidone ranging from K15 to K120.

2. Pharmaceutical solutions of claim 1 wherein the calcitonin is human calcitonin, eel calcitonin, carbocalcitonin (elcatonin), chicken calcitonin or porcine calcitonin.

3. Pharmaceutical solutions of claim 1 wherein the polyvinyl-pyrrolidone is of the type K40.

4. Pharmaceutical solutions of claim 1 comprising:
   a) the calcitonin or its pharmaceutically acceptable salts in concentrations of 250 I.U./ml to 5,000 I.U./ml;
   b) the N-(methyl)-glucamine or glucamine in concentrations of 2.0 to 5.0 mg/ml;
   c) the tromethamine in concentrations of 1.0 to 4.0 mg/ml;
   d) the citric acid in concentrations of 5.0 to 9.0 mg/ml; and e) the polyvinylpyrrolidone ranging from K15 to K120 in concentrations of 5 to 25 mg/ml.

5. Pharmaceutical solutions of claim 1 wherein the concentration of the calcitonin or its pharmaceutically acceptable salts is from 400 I.U. to 1,200 I.U./ml.

6. Pharmaceutical solutions of claim 1 wherein the concentration of the N-(methyl)-glucamine or glucamine is from 2.5 to 4.0 mg/ml.

7. Pharmaceutical solutions of claim 1 wherein the concentration of tromethamine is from 1.5 to 2.5 mg/ml.

8. Pharmaceutical solutions of claim 1 wherein the concentration of the citric acid is from 6.0 to 8.0 mg/ml.

9. Pharmaceutical solutions of claim 1 wherein the concentration of the polyvinylpyrrolidone ranging from K15 to K120 is from 8 to 15 mg/ml.

10. Pharmaceutical solutions of claim 1 wherein the solutions are sterile formulations.

11. Pharmaceutical solutions of claim 1 wherein the solutions contain one or more $C_{1-4}$ alkylesters of p-hydroxybenzoic acid.

12. Pharmaceutical solutions of claim 11 wherein the $C_{1-4}$ alkylesters of p-hydroxybenzoic acid are methyl p-hydroxy benzoate or propyl p-hydroxy and mixtures thereof.

13. Pharmaceutical solutions of claim 1 having pH values of from 4.6 to 6.0.

14. Pharmaceutical solutions of claim 1 having pH values of from 5.0 to 5.9.

15. Pharmaceutical solutions of claim 1 comprising:

$1 \times 10^3$ I.U./ml of salmon calcitonin as acetate salt;

3.33 mg/ml of N-(methyl)-glucamine or glucamine;

2.10 mg/ml of tromethamine;

6.82 mg/ml of citric acid;

10.00 mg/ml of polyvinylpyrrolidone;

1.00 mg/ml of methyl p-hydroxy benzoate;

0.10 mg/ml of propyl p-hydroxy benzoate; and 976.65 mg/ml of water.

16. Pharamecutical solutions of claim 1 comprising:

$2 \times 10^3$ I.U./ml of salmon calcitonin as acetate salt;

3.33 mg/ml of N-(methyl)-glucamine or glucamine;

2.10 mg/ml of tromethamine;

6.82 mg/ml of citric acid;

10.00 mg/ml of polyvinylpyrrolidone;

1.00 mg/ml of methyl p-hydroxy benzoate;

0.10 mg/ml of propyl p-hydroxy benzoate; and 976.65 mg/ml of water.

17. Pharmaceutical solutions of claim 1 comprising:

400 I.U./ml of elcatonin;

3.33 mg/ml of N-(methyl)-glucamine;

2.10 mg/ml of tromethamine;

6.82 mg/ml of citric acid;

10.00 mg/ml of polyvinylpyrrolidone;

1.00 mg/ml of methyl p-hydroxy benzoate;

0.10 mg/ml of propyl p-hydroxy benzoate; and 976.65 mg/ml of water.

18. Pharmaceutical solutions of claim 1 having enhanced organoleptic character.

19. Pharmaceutical solutions of claim 1 wherein the polyvinylpyrrolidone prolongs the time of contact between the solution and nasal mucosa.

20. Pharmaceutical solutions of claim 1 comprising salmon calcitonin, characterized in that the solutions produce, during 18 months of storage, at most minor quantities of hydroxy-calcitonin.

21. Pharmaceutical solutions of claim 1 comprising salmon calcitonin wherein the solutions present, during 18 months of storage, substantially less than 5 wt % degradation products.

22. Pharmaceutical solutions of claim 1 wherein said solutions are without any inorganic components.

23. A method of using pharmaceutical solutions according to claim 1 in conventional analytical methods to determine the quantity of acetic acid contained, as volatile impurity, in calcitonin salmon active ingredient or any other natural or modified calcitonin as acetate used for their preparation.

24. Pharmaceutical solutions of claim 1 wherein the calcitonin comprises carbocalcitonin.

25. A method of using pharmaceutical solutions of claim 1 for the preparation of medicinal products suitable for endonasal administration for treatment of osteoporosis.

* * * * *

UNITED STATES PATENT AND TRADEMARK OFFICE
CERTIFICATE OF CORRECTION

PATENT NO. : 6,087,338
DATED : July 11, 2000
INVENTOR(S) : Paolo A. Veronesi et al.

It is certified that error appears in the above-identified patent and that said Letters Patent is hereby corrected as shown below:

Claim 23 should read as follows:
-- Pharmaceutical solutions of claim 1 wherein the calcitonin comprises salmon calcitonin. --.

Signed and Sealed this

Twenty-fifth Day of September, 2001

Attest:

*Nicholas P. Godici*

NICHOLAS P. GODICI
*Attesting Officer*    *Acting Director of the United States Patent and Trademark Office*